United States Patent [19]

Poindexter

[11] 4,416,818

[45] Nov. 22, 1983

[54] PREPARATION OF N-ALKOXYCARBONYL-SUBSTITUTED CYCLIC LACTAMS AND KETONES

[75] Inventor: Graham S. Poindexter, Evansville, Ind.

[73] Assignee: The Dow Chemical Company, Midland, Mich.

[21] Appl. No.: 309,958

[22] Filed: Oct. 9, 1981

[51] Int. Cl.³ .................. C07D 210/00; C07D 207/12
[52] U.S. Cl. ............................ 260/239.3 A; 548/230; 548/531; 546/245
[58] Field of Search .............. 548/230; 260/239.3 A, 260/326.45; 546/245

[56] References Cited

U.S. PATENT DOCUMENTS 4,130,563 12/1978 Scholz et al. ..................... 548/230
4,186,129 1/1980 Huth et al. ........................ 548/231

FOREIGN PATENT DOCUMENTS 1343585 1/1974 United Kingdom ............... 424/272

OTHER PUBLICATIONS

Joullie, M. M. et al., JACS, 76, 2990, (1954).
Pierce, et al., J.O.C., 28, 658, (1963).
Blicke, F. F. et al., JACS, 74, 3933, (1952).
Satchell, D. P. N., Quart. Rev., 17, 160–163, 184–191 (1963).

Primary Examiner—Donald G. Daus
Assistant Examiner—S. A. Gibson
Attorney, Agent, or Firm—Douglas D. Deline

[57] ABSTRACT

N-alkoxycarbonyl-substituted cyclic lactams and nitrogen-containing cyclic ketones are prepared by reaction of a $C_{1-20}$ alkyl ester of trichloroacetic acid with the corresponding cyclic lactam or nitrogen-containing cyclic ketone.

6 Claims, No Drawings

PREPARATION OF N-ALKOXYCARBONYL-SUBSTITUTED CYCLIC LACTAMS AND KETONES

BACKGROUND OF THE INVENTION

This invention relates to a novel process for preparing N-alkoxycarbonyl-substituted cyclic lactams and ketones by the reaction of an alkyl ester of trichloroacetic acid with the corresponding cyclic lactam or nitrogen-containing cyclic ketone. The products are useful as intermediates in the synthesis of isocyanates and the preparation of other useful chemicals.

It is previously known to react ethyl chloroformate with 2-oxazolidinone in the presence of an equivalent amount of triethylamine. Y. A. Naumov et al., *Khim. Geterotsikl. Soedin.*, 768 (1976) (*Chem. Abs.*, 85, 123067q 1976). The process is not preferred for commercial implementation due to the unavoidable formation of large amounts of salt during the process according to the following equation.

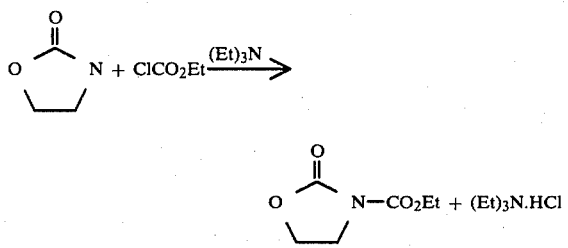

Therefore an alternate procedure to useful chemical intermediates such as this is desirable.

SUMMARY OF THE INVENTION

A novel process has now been discovered for the preparation of N-alkoxycarbonyl-substituted cyclic lactams and ketones represented by the formula:

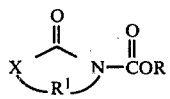
(I)

where X is oxygen or methylene, R' is $C_{2-4}$ alkylene and R is $C_{1-20}$ alkyl, which comprises reacting a $C_{1-20}$ alkyl ester of trichloroacetic acid with a cyclic lactam or nitrogen-containing cyclic ketone of the formula:

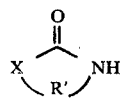

where X, R' and R are as previously defined. Preferred ester reactants are $C_{1-4}$ alkyl esters of trichloroacetic acid. Most preferred is ethyl trichloroacetate. Preferred cyclic lactam or nitrogen-containing cyclic ketone reactants include 2-oxazolidinone, 2-pyrrolidinone or caprolactam. Most preferred is 2-oxazolidinone.

The by-product, chloroform, is easily separated from the desired cyclic ester derivative and is itself commercially valuable.

DETAILED DESCRIPTION OF THE INVENTION

The reaction is conducted by contacting the desired reactants at an elevated temperature preferably in the presence of a suitable acylation catalyst. The reaction is suitably conducted in reaction vessels of ordinary design and construction. Temperatures from about 100° C. to about 160° C. are suitable. Preferred temperatures are from about 105° C.–125° C.

A preferred acylation catalyst is 4-dimethylaminopyridine. The catalyst is added in a catalytically effective amount from about 0.01 percent to about 10 percent by weight.

Elevated pressures may be employed if desired, however, no advantage is known to arise therefrom. Suitable reaction rates are obtained without the use of superatmospheric pressure.

Molar ratios of cyclic lactam or nitrogen-containing cyclic ketone to trichloroacetic acid ester of from about 1:1 to about 1:30 may suitably be employed. Preferably an excess of the $C_{1-20}$ alkyl ester of trichloroacetic acid is employed.

Reaction times may vary from a few minutes to several hours, depending on the temperature of the reaction and the alkyl ester employed. Separation of the product is easily accomplished by ordinary techniques such as distillation.

SPECIFIC EMBODIMENTS

Having described my invention, the following examples are provided as further illustrative of the present invention.

EXAMPLE 1

Preparation of 3-Carboethoxy-2-Oxazolidinone

A mixture of 2-oxazolidinone (9.0 g, 0.10 mole) and 25 ml (0.18 mole) of ethyl trichloroacetate were heated to 120° C. in an oil bath. A small amount (ca 50 mg) of 4-dimethylaminopyridine was added to the stirred solution, during which time vigorous reflux began. After removing most of the chloroform by a Dean-Stark trap, the dark solution was allowed to cool to room temperature. Bulb to bulb distillation at 105° C.–120° C. (0.05 mm) yielded 14.1 g (0.0887 mole, 89 percent yield) of the product as a clear liquid which solidified to a colorless solid (mp 40° C.–44° C.) on standing at room temperature. Spectral data confirmed its structure.

EXAMPLE 2

Preparation of N-Carboethoxy-2-Pyrrolidinone

In a manner similar to the above procedure, a solution of 2-pyrrolidinone (9.1 g, 0.11 mole), ethyl trichloroacetate (140 ml, 2.9 mole) and catalytic amounts of 4-dimethylaminopyridine were reacted together for 1 hour. Distillation at 90° C.–95° C. (0.4 mm) afforded 14.2 g (0.094 mole, 82 percent yield) of the product as a clear liquid. Spectral data confirmed its structure.

What is claimed is:

1. A process for preparing N-alkoxycarbonyl-substituted cyclic lactams and nitrogen-containing cyclic ketones of the formula

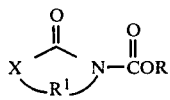

where X is oxygen or methylene, R' is $C_{2-4}$ alkylene and R is $C_{1-20}$ alkyl comprising reacting a $C_{1-20}$ alkyl ester of trichloroacetic acid with a cyclic lactam or nitrogen-containing cyclic ketone of the formula

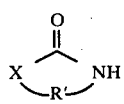

where X and R' are as previously defined, at a temperature from about 100° C. to about 160° C. in the presence of a catalytically effective amount of an acylation catalyst.

2. The process according to claim 1 wherein the catalyst is 4-dimethylaminopyridine.

3. The process according to claim 1 wherein one reactant is a $C_{1-4}$ alkyl ester of trichloroacetic acid.

4. The process according to claim 3 wherein one reactant is ethyl trichloroacetate.

5. The process according to claim 1 wherein the cyclic lactam or nitrogen-containing cyclic ketone is 2-oxazolidinone, 2-pyrrolidinone or caprolactam.

6. The process of claim 5 wherein the cyclic lactam or nitrogen-containing cyclic ketone is 2-oxazolidinone.

* * * * *